(12) United States Patent
Smith et al.

(10) Patent No.: US 6,968,301 B1
(45) Date of Patent: Nov. 22, 2005

(54) METHOD FOR ANALYSIS OF BIOLOGICAL SYSTEMS

(76) Inventors: David Smith, 4 Sakonia Close, Wallsend, New South Wales 2287 (AU); Roger Smith, 56 Memorial Drive, New Castle, New South Wales 2300 (AU)

( * ) Notice: Subject to any disclaimer, the term of this patent is extended or adjusted under 35 U.S.C. 154(b) by 0 days.

(21) Appl. No.: 09/744,291

(22) PCT Filed: Jul. 23, 1999

(86) PCT No.: PCT/AU99/00597

§ 371 (c)(1),
(2), (4) Date: Apr. 4, 2001

(87) PCT Pub. No.: WO00/05671

PCT Pub. Date: Feb. 3, 2000

(30) Foreign Application Priority Data

Jul. 23, 1998 (AU) ...................... PP6634

(51) Int. Cl.⁷ .......................... G06G 7/48; G01N 33/48
(52) U.S. Cl. ................... 703/11; 703/2; 703/6; 702/19; 706/21; 706/934
(58) Field of Search ................. 703/11, 2, 6; 702/19; 706/21, 934

(56) References Cited

U.S. PATENT DOCUMENTS 3,628,904 A * 12/1971 Canguilhem .................. 705/7

OTHER PUBLICATIONS

Maguire Jr., B. Ecosystem simulation through use of models of subsystem response structures. Simulation, 1974, vol. 23, No. 5, pp. 149-158.*

Yagyu et al, Globql Dimensional Complexity of Multichannel EEG in Mild Alzheimer's Disease and Age-Matched Cohorts; Dementia and Geriatic Cognitive Disorders, 1997, Vo. 8. No. 6. pp. 343-347.

Bastiannssen et al, State-Space Ananlyssis of a Myocybernetic Model of the Lower Urinary Tract, Journal of Theoretical Biology, Jun. 7, 1996, vol. 180 (3), pp. 215-227.

Witt, Multichannel Evoked Potentials as Voltage Space Trajectories; Mathematical Biosciences, Dec. 1994, vol. 124 (2), pp. 207-224.

Kaplan, Geometrical Techniques for Analyzing ECG Dynamics; Journal of Electrocardiology, 1992, vol. 24 (Supplement) pp. 77-82.

Eisenhammer et al, Modeling Experimental Time Series with Ordinary Differenttial Equations, Biological Cybernetics, 1991, vol. 65, No. 2, pp. 107-112.

Park et al, Mathematical Modeling of Differentiation in Dictyosteilum Discoideum, Molecular & Cellular Biochemistry, Aug. 31, 1975, vol. 8, No. 2.

* cited by examiner

*Primary Examiner*—Mary K. Zeman
(74) *Attorney, Agent, or Firm*—Jon Carl Gealow (57) ABSTRACT

A method of analyzing an evolution of a biological system comprising the steps of determining a series of variables upon which a state of the biological system depends, mapping the variables to an n-dimensional space, and wherein the evolution of the biological system is monitored utilising a trajectory formed from sets of the variables which define the states of the biological system at different times, thereby using time as a parameter in the n-dimensional space in a manner such that every point on the trajectory corresponds to at least one value of time.

13 Claims, 4 Drawing Sheets

METHOD FOR ANALYSIS OF BIOLOGICAL SYSTEMS

FIELD OF THE INVENTION

The present invention relates to the organisation and interpretation of data relating to biological systems. The invention will be described hereinafter in the context of medical research/clinical management of patients, i.e. using medical terminology, but it will be understood that the present invention does have broader applications to biological systems in general.

BACKGROUND OF THE INVENTION

In medical research and monitoring of patient behaviour it is currently the usual approach to "pool" data, i.e. to base an analysis on trends derived by averaging particular data obtained from a large number of patients in a suitable way. It is further common to limit an evaluation of a patient's behaviour to one variable at a time, i.e. the development of a particular variable is followed over time and, for example, charts illustrating the development are used to assist the practitioner in his assessment of the patient behaviour. This has several disadvantages.

For example, the reliance upon averaged data in evaluating the patient behaviour somewhat limits the spectrum of the assessment made as extreme values on opposite sides of the average are effectively cancelled out of consideration in the assessment. Another disadvantage is that this "one variable at a time" approach makes it more difficult for the practitioner to remain alert to various other variables which could form a complex interrelationship with the particular variable when evaluating the patient behaviour. This is not to say that practitioners in general are not alert to this problem, but the likelihood of not taking into consideration all necessary variables is increased.

In current medical practice one variable at a time (e.g. temperature) is plotted against time. Time appears as an independent variable typically along the X-axis and e.g. temperature along the Y-axis. Many such separate two-dimensional graphs are used to plot various variables such as blood pressure against time, urinary volume against time, heart rate against time etc., each variable being depicted on a separate graph. Up to now, the use of time as the independent variable plotted along one axis of the graph somewhat dictates the preferred use of a multiplicity of two-dimensional graphs when managing medical data.

In contrast, it is known that physicists employ a set of variables to describe the behaviour of a particular system in a three-dimensional space. A well-known example that is a paradigm for the scientific method is provided by the behaviour of an ideal gas. In this case the variables are pressure, volume and temperature and together they define a three-dimensional space. Those variables are related by the well known "equation of state for an ideal gas"

$$PV = nRT.$$

In this equation n is the number of moles of gas present in the system and R is the universal gas constant. This equation may be represented as a surface in the three-dimensional space and represents each "allowed" state of an ideal gas in those three dimensions.

SUMMARY OF THE INVENTION

At least preferred embodiments of the present invention can enhance the management and interpretation of data relating to a biological system to thereby improve e.g. the assessment capabilities of a non-specialist doctor.

In accordance with a first aspect of the present invention there is provided a method of analysing an evolution of a biological system comprising the steps of determining a series of variables upon which a state of the biological system depends, mapping the variables to an n-dimensional space, wherein the evolution of the biological system is monitored utilising a trajectory formed from sets of the variables which define the states of the biological system at different times, thereby using time as a parameter in the n-dimensional space in a manner such that every point on the trajectory corresponds to at least one value of time; and evaluating the evolution of the biological system utilising sets of predetermined values of the variables to formulate an n-dimensional surface representing a predetermined state of the biological system within the n-dimensional space.

In that way, time is used as a "hidden" variable to analyse the evolution of the biological system, which can facilitate an improved method of analysing the evolution of the biological system in which the interrelationship between the variables upon which the state of the biological system depends can become more apparent.

Preferably, n is an integer greater than 2.

In one embodiment, the step of evaluating the evolution of the biological system comprises predicting a progression of the trajectory.

Preferably, the prediction of the progression of the trajectory is based on the previous development of the trajectory within the n-dimensional space.

In another embodiment, the prediction of the progression of the trajectory is based on other trajectories determined in the n-dimensional space.

In accordance with a second aspect of the present invention there is provided a method of representing a predetermined state of a biological system comprising the steps of determining a series of variables upon which the predetermined state of the biological system depends, mapping the variables to an n-dimensional space and utilising sets of predetermined values of the variables to formulate an n-dimensional surface describing the predetermined state within the n-dimensional space.

In accordance with a third aspect of the present invention there is provided a computer arranged to analyse an evolution of a biological system based on a series of variables upon which a state of the biological system depends, the computer being arranged to map the variables to an n-dimensional space, and to monitor the evolution of the biological system based on a trajectory formed from sets of the variables which define the states of the biological system at different times; and evaluate the evolution of the biological system utilising sets of predetermined values of the variables to formulate an n-dimensional surface representing a predetermined state of the biological system within the n-dimensional space.

In accordance with a fourth aspect of the present invention there is provided a computer arranged to represent a predetermined state of a biological system based on a series of variables upon which the predetermined state of the biological system depends, the computer being arranged to map the variables to an n-dimensional space and to formulate an n-dimensional surface describing the predetermined state within the n-dimensional space, based on sets of predetermined values of the variables.

In accordance with a fifth aspect of the present invention there is provided a computer readable storage medium comprising instructions to control a computer to analyse an evolution of a biological system based on series of variables upon which a state of the biological system depends, the instructions comprising instruction to control the computer to map the variables to an n-dimensional space; and monitor the evolution of the biological system based on a trajectory formed from sets of the variables which define the states of the biological system at different times; and evaluate the evolution of the biological system utilising sets of predetermined values of the variables to formulate an n-dimensional surface representing a predetermined state of the biological system within the n-dimensional space.

In accordance with a sixth aspect of the present invention there is provided a computer readable storage medium comprising instructions to control a computer to represent a predetermined state of a biological system based on a series of variables upon which the predetermined state of the biological system depends, the instructions comprising instructions to control the computer to map the variables to an n-dimensional space; and formulate an n-dimensional surface describing the predetermined state within the n-dimensional space, based on sets of predetermined values of the variables.

The present invention may be applicable, but is not restricted to use in a clinical context, in medical research and in medical training. The medical training can comprise both medical training of persons in the medical profession and training/developing a better patient's understanding.

Embodiments of the invention may play an important role in assisting patients to understand, firstly, what is wrong. For example, they may be moving along a trajectory that is likely to lead to a disease state, such as cardiovascular disease. Secondly, they may assist patients to then appreciate what has to be done to ensure a healthy state is maintained or regained. This could be a valuable tool facilitating doctor-patient relationships and improving patient compliance with the proposed treatment regime.

Embodiments of the invention may be employed as valuable educative tool when training health professionals. The concept of a state-space, current location in the state-space and proximity to various limit-states is a valuable method for representing normality and disease and this may facilitate the education of medical professionals. The conceptual framework of the invention can be presented graphically. Details of how this can be done can be found in the description of preferred embodiments of the invention. All disease states may be viewed as a movement toward some particular limit-state surface in some state-space. The signs and symptoms of disease may be viewed as particular locations in a state-space in relation to suitably chosen limit-state surfaces.

An important part of the medical interview is the patient history. In the context of the invention as described here, this history may be interpreted as the patient's perception of their proximity to various limit-state surfaces. This information may be incorporated into embodiments of the invention in a semi-quantitative way (ie. by employing a magnitude on some appropriate scale and limit-state surfaces at appropriate locations in the state-space).

With the assistance of a suitable computer program, the systematic evaluation of various treatment scenarios could be examined in a clinical environment by the treating physician but may also be used in controlled learning environment using the model, in much the same way as pilots are trained using a flight simulator by an instructor. It will be understood by a person skilled in the art that known techniques such as the use of neural networks may be utilised in improving the reliability of simulations.

The invention is also potentially useful in assessing the cost of various treatment alternatives if used in conjunction with a suitable cost database. The model may be a very valuable tool for the allocation of scarce resources by medical management.

The mathematical model used in embodiments of the invention may be 'customised' by experts in the field, reflecting their particular understanding of a subject.

In some cases, previous medical conditions may have lead to realisation of a specific condition (eg. a previous pregnancy, or previous hospitalisation for asthma treatment). This patient specific information may also be incorporated in the model to improve the predictive capability of the model for that particular patient. Hence, a valuable component of a patients' medical record may be an interpretation of their medical history in terms of the mathematical model described here.

BRIEF DESCRIPTION OF THE DRAWINGS

The invention may be more fully understood from the description of preferred forms given below with reference to the accompanying drawings, by way of example only.

In the drawings.

DESCRIPTION OF A PREFERRED EMBODIMENT

The embodiments of the invention will be described by way of reference to a number of initial examples. However, the scope of the present invention is not limited to these examples. To further illustrate the broader application of the invention, in the following a particular terminology is introduced in which terms are defined in a conceptional sense and then particular examples are given in which the conceptional terms are correlated with specific systems.

The conceptional basis for the invention is the analysis of a biological system, for example the physiological states in humans, in a multi-dimensional state-space. The dimensions of the state space are correlated with parameters/variables which influence the biological system, i.e. which influence the state of the biological system in respect of the state-space. The behaviour of the biological system can thus be described as the evolution of the state of the system within the state-space over time, i.e. a trajectory of the biological system is monitored and from it the current state of the system can be known. Importantly, provided the state space is chosen correctly, certain states of the biological system within the state-space will be attributable to certain biological events, i.e. the biological state of the system has reached a particular limit-state. Particular examples for limit-states are given below. Generally speaking a limit state is the realisation of a biologically or medically defined state of the system, both normal and abnormal states. As various combinations of different parameters can lead to the realisation of a particular limit-state, the limit-state can be described as a function within the state-space. The relative positioning of the trajectory of a biological system and a limit-state surface within the state-space can form the basis for the development of a systematic method for both differential diagnosis and for patient management. The use of the method for differential diagnosis may form the basis of information structuring in an 'expert system' for the purpose of medical differential diagnosis.

The state-space variables may be normalised (non-dimensionalised) by various methods, each method of normalisation resulting in a different depiction of the trajectories and limit surfaces in the normalised state-space.

One normalisation method can reduce a trajectory to a point in the normalised state-space. If the trajectory that is reduced to a point in the normalised state-space is the mean (or median or mode) trajectory, then trajectories in the normalised state-space will represent departures from this mean (or median or mode) trajectory.

In the following, examples of preferred embodiments of the invention will be described with reference to the physiological states in humans.

EXAMPLE I

Analysis of Physiology of Pregnancy

A first example relates to the analysis of pregnancy in women. Pregnancy is distinguished by one very obvious event, giving birth. It is practice to regularly monitor women over the course of the pregnancy, thereby facilitating the monitoring of several parameters during that period.

A careful consideration leads to the initial proposal of the following 'simple' state-space for the assessment of pregnancy. The state-space variables chosen for plotting the trajectories are corticotrophin-releasing-hormone concentration (CRH), oxytocin concentration (OT), progesterone concentration (P), oestrodiol concentration (E), cortisol concentration (C), cervical stiffness (CS) and stretch of the smooth muscle fibres within the uterus (S). S may be a dependent variable from independent variables which could include such quantities as volume of the amniotic fluid and fetal mass. CRH may be a dependent variable from independent variables which could include such quantities as placental mass, maternal blood volume and concentration of maternal CRH binding protein. Other independent variables may also be specified in turn for each of the remaining five state variables.

There may be other known state-variables (eg. relaxin, prostaglandins) or as yet unknown state-variables of importance. It is further observed that failure of the model to achieve the desired reliability could suggest the presence of additional, as yet unknown factors.

The limit-states that may be of interest for the analysis of pregnancy include 'uterine contractions leading to birth', 'cervical competence' and 'fetal lung maturation'. Only 'uterine contractions leading to birth' will be pursued here as an example. All the state-variables except CS will be employed as state-variables for the analysis of this limit-state.

There are six state variables employed here in the consideration of the 'uterine contractions leading to birth' limit state analysis. Those may be grouped into two state-subspaces, with each state-subspace involving three state-variables (see FIGS. 1 and 2).

Figure 1:
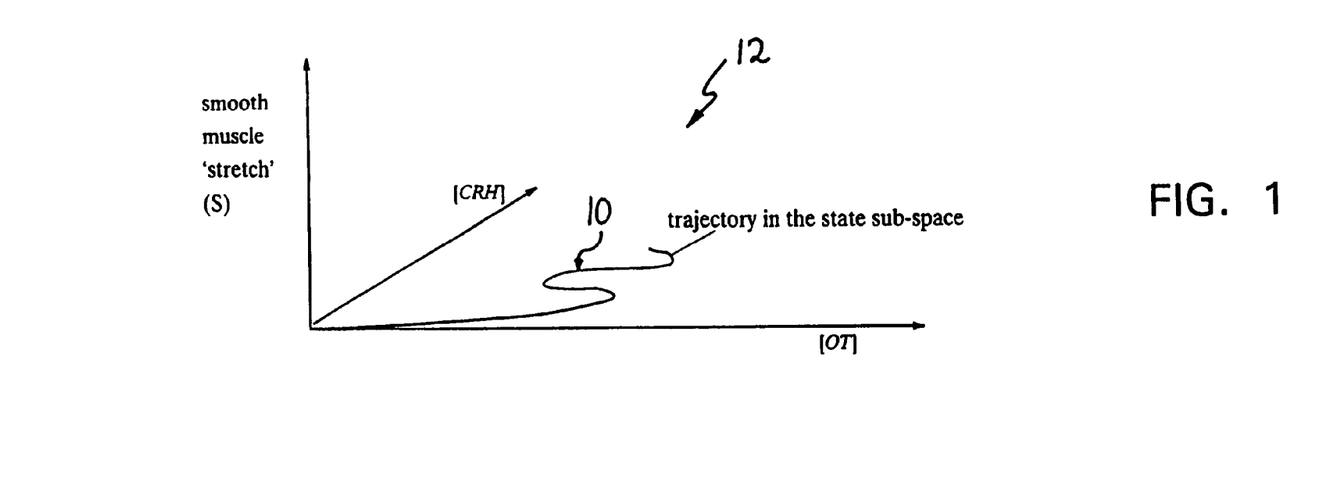
FIG. 1 illustrates a state subspace with a trajectory of a patient behaviour in accordance with an embodiment of the present invention.
Figure 2:
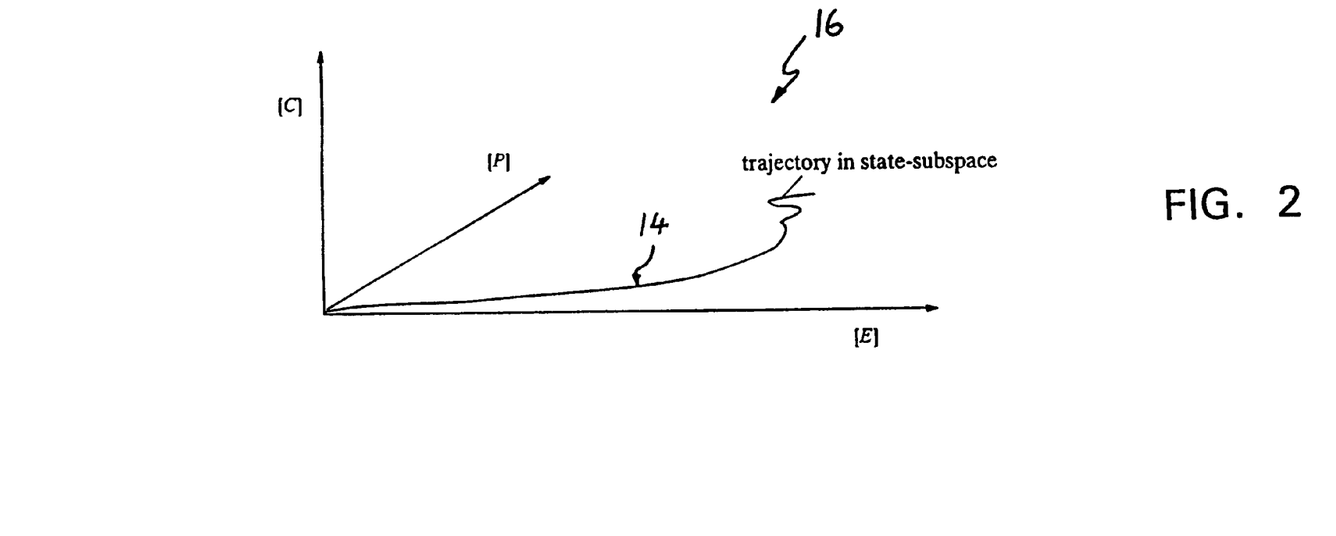
FIG. 2 illustrates another state subspace with trajectory of a patient behaviour in that state subspace.

A first trajectory 10 in a first state-subspace 12 is sketched in FIG. 1 and a second trajectory 14 in state-subspace 16 is sketched in FIG. 2. While the grouping of state-variables may be arbitrary, there may be reasons for choosing one grouping of variables over another. For example, state-variables may be grouped according to clinical importance.

It is seen that the first trajectory 10 in the first state-subspace 12 (FIG. 1) oscillates throughout pregnancy due to diurnal fluctuations in the concentration of oxytocin. There may be normal and or abnormal (ie. pathologic) trajectories in this state-subspace. Normal and abnormal behaviours along the CRH axis leading to pre-term, term and post-term parturition have already been identified by the research investigations of Mark McLean, Andrew Bisets, Joanne Davies, Russel Woods, Philip Lowry and Roger Smith (May, 1995), 'A placental clock controlling the length of human pregnancy', Nature Medicine, Vol. 1 No. 5 p. 460–463).

It is seen that the second trajectory 14 in FIG. 2 also oscillates late in pregnancy due to diurnal fluctuations in the concentration of E and P. (It is noted here that the E/P ratio may be a more appropriate state-subspace variable, rather than E and P separately). Once again, there may be normal and/or abnormal (ie. pathologic) trajectories in this state-subspace.

Figure 3:
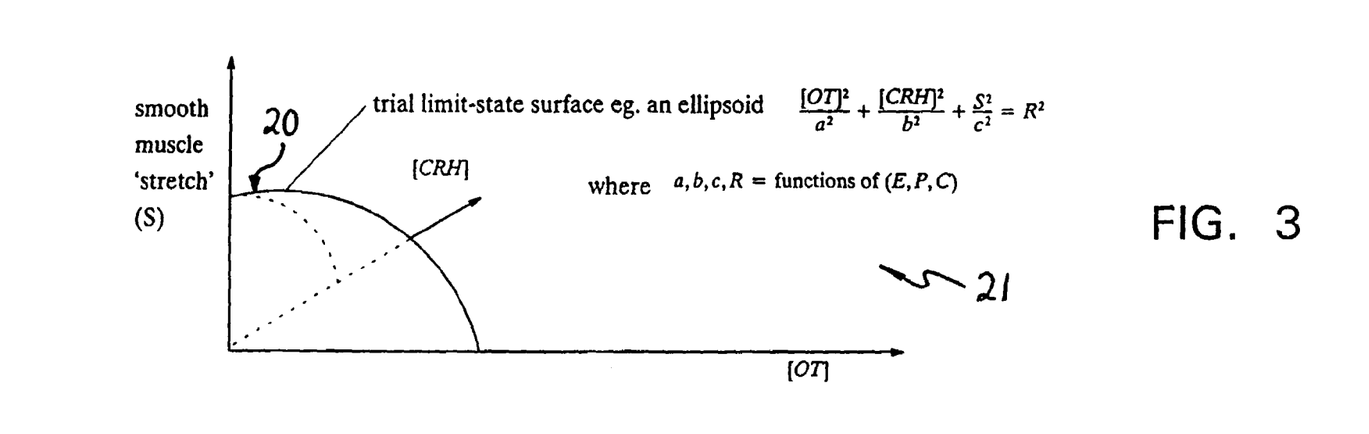
FIG. 3 illustrates the state subspace of FIG. 1 with a trial limit-state function describing the occurrence of an event in that state subspace.

The limit-state surface (not shown) in both state-subspaces may evolve (change position) over time. This is due to the fact that the limit-state surface is dependent on variables which are themselves time dependent. A third limit-state surface 20 in one state-subspace 21 (CRH, OT and S), at one particular time, is shown in FIG. 3.

It is well known that the processes leading to pregnancy contain redundancies. By this it is meant that some state-variables may not be essential for a normal birth. In other words, a redundant state-variable may be important when present, yet non-essential to a normal birth. It is noted that the described redundancy of state-variables observed during pregnancy is made immediately visually clear by the ellipsoidal shaped limit-state surface proposed here. For example, if CRH is absent (or present in abnormal very low concentrations), then the state-subspace in FIG. 3 is reduced to two dimensions, and a women's trajectory in the state-subspace will be confined to a 'plane' in the state-subspace. It is immediately visually apparent that the trajectory confined to this plane can still intersect the limit-state surface. This intersection of trajectory and limit-state surface indicates that progression to birth is still possible.

To better visually comprehend the trajectories of pregnant women in the state-space, it may be advantageous to have the two state-subspaces depicted simultaneously on a computer screen. Time could also be indicated along each trajectory by 'tick' marks. Speed along the trajectory may be indicated by a line of varying thickness, or colour or gradient markers. It is noted in passing that the time lapsed since conception can be accurately measured using ultra-sonic techniques.

It is probable that the limit-state surface in each state-subspace expands (moves away from the origin) early in pregnancy (due to it being dependent on state variables), and may contract and then oscillate later in pregnancy, thereby precipitating parturition. The oscillation of the trajectory and the limit-state subspace surface is believed to be 'phase locked' (ie. the trajectory in a state-subspace moves away from the origin at the same time as the limit-state surface moves toward the origin). This simple observation, easily visually comprehended using the methods described here, may explain why the initiation of births occur during the night due to a periodical contraction of the limit-state surface during night time.

Now that the limit-state surface is known to be important, the 'shape' of the state surface in a state-subspace may be actively 'probed' by selected tracking of individual women throughout pregnancy. As this data becomes available, it is expected that the trial limit state surface 20 shown in FIG. 3 will be modified. This procedure will define normal and abnormal trajectories in the state-space, as well as the shape of the limit-state surface. This empirical approach to define the limit-state surface and trajectories in the state-space may be supplemented when possible by detailed physiological and biochemical models. This method of investigating pregnancy is an example of how the mathematical method described here can be utilised in medical research.

Figure 4:
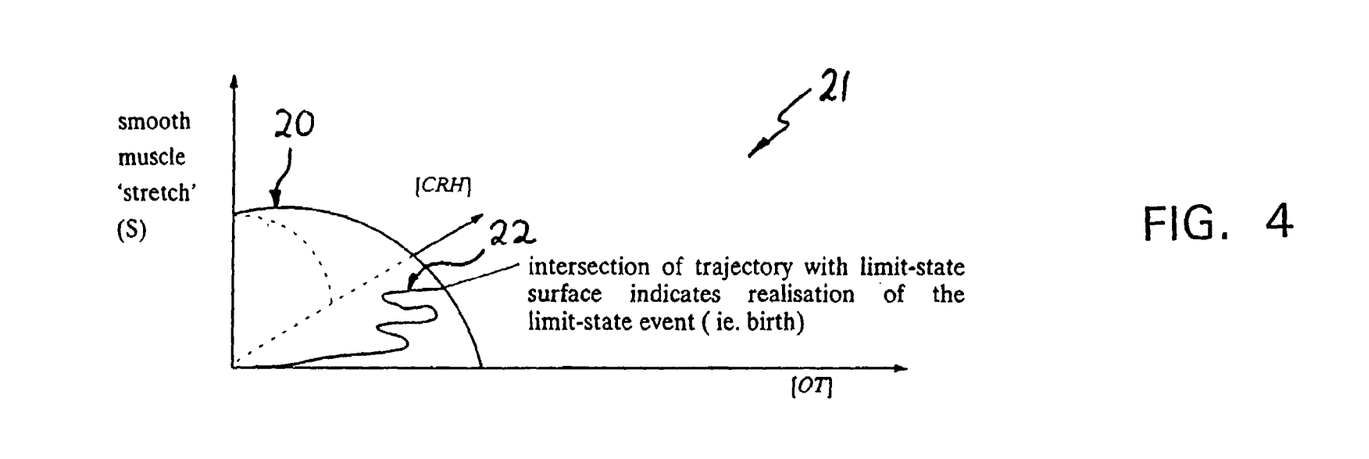
FIG. 4 illustrates the state subspace of FIG. 3 with the trajectory of the patient behaviour of FIG. 1.

The onset of uterine contractions leading to birth occurs when the trajectory 22 in the 'state-space' 21 intersects the limit-state surface 20. This is shown in the FIG. 4. It is clearly advantageous for defining the limit-state surface, to monitor the trajectory accurately close to the time of birth, and preferably obtain a point in the state-space at the time of birth (ie. on the limit-state surface). However, if this is not possible, it is believed that it may be possible to reliably extrapolate the trajectory in the state-space to the time of birth, given adequate previous knowledge of the trajectory in the state-space and knowledge of the underlying physiological and biochemical processes.

EXAMPLE II

Predictive Analysis

The embodiment described above has been described in a deterministic format. However, a statistical analysis of the current location in a state-subspace in relation to the limit-state surface can be easily incorporated in another embodiment. This could be implemented in various ways, a Monte-Carlo simulation being one of the most general method applicable. This embodiment could then be employed to make predictions of the type 'there is a 90% chance that a pre-term delivery will occur'.

It is noted that the effect of a proposed course of medical intervention could be quantitatively assessed by the embodiment described. For example, the likely effect of intervention by a clinician using a CRH antagonist could be shown in the state-space. As there may be several ways of achieving the desired outcome (ie. realisation of the limit state event, or moving away from the limit-state event), alternative treatment methods could be assessed before they are implemented by a clinician. The distance between the current state and the limit-state surface, in conjunction with probability density functions, will give a quantitative measure of likelihood of success or otherwise of the proposed intervention.

It is noted that the distance of interest may not be the 'shortest distance' between the current position in the state-space and the limit-state surface, but could depend on an individual's trajectory in the state-space. If the trajectory is well-defined (ie. both direction and speed is known, or can be estimated), it may be possible to reliably extrapolate from the current position in the state-spate to some future position in the state-space. If the speed along the trajectory is known, or can be reliably estimated on the basis of past experience, then the time to realise the limit-state event could be reliably estimated. In other words, the time of birth could be reliably predicted.

The embodiments described above could be presented as a computer program that is employed as an aid to clinicians in management of their patients. Normal and abnormal trajectories in each state-subspace could be displayed in different colours. This method could then be employed as a valuable predictor of abnormal pregnancy states. Normal and abnormal limit-state surfaces could also be displayed in different shadings. Multiple limit-state surfaces could be depicted in different colours, and highlighted by a 'light source' strategically located in relation to the observer. When multiple limit-state surfaces are depicted, only the 'closest' limit-state surfaces in relation to the current position may be displayed, thereby assisting visual clarity of the problem. Optimal or 'target' positions may be marked on a limit-state surface.

The time evolution of the trajectory and limit-state surfaces in the state-subspace could be animated to enhance understanding of the dynamic nature of the system. 'Zooming' and 'rotating' the computer image to position the viewer's vantage point at right-angles to the trajectory may facilitate comprehension of the situation. In other circumstances, rotating the viewer's vantage point to be at right angles in the limit-state surface at the anticipated interception point of the trajectory with the limit-state surface may be helpful in interpreting the results of the mathematical model (eg. viewing the marginal probability distributions).

Several state-subspaces may be viewed simultaneously on a divided computer screen. Investigation of treatment alternatives by a clinician could be made by 'clicking' and 'dragging' the current position in a state-space to a new position in the state-space, this new position representing the effect of intervention. This 'virtual' intervention could then be assessed by computing updated positions of the limit-state surfaces in the multi-dimensional space. Graphically, this would be seen by the analyst as a limit-state surface 'swinging around' in the state-space. The clinician could be alerted to any intersections of trajectories and limit-state surfaces. The clinician could select the level of probability of realising a limit-state, and only those limit-states with a greater probability of occurrence would be brought to the attention of the clinician by a warning appearing on the screen.

It is often the case that limit-state surfaces are smooth, continuous, differentiable functions in the state-space. Further, it is often the case that a limit-state surface may be a finite 'patch' in the state-subspace (having a finite 'height' and 'length'), due to the range of biologically achievable values for the state variables being limited.

The state-space may have intersecting multi-dimensional limit-state surfaces. The intersection of limit-state surfaces is attributed to simultaneous satisfaction of several limit-states. For simultaneous realisation of several limit-states, the trajectory in the state-space must intersect the limit-state surfaces at one point see FIG. 5.

Figure 5:
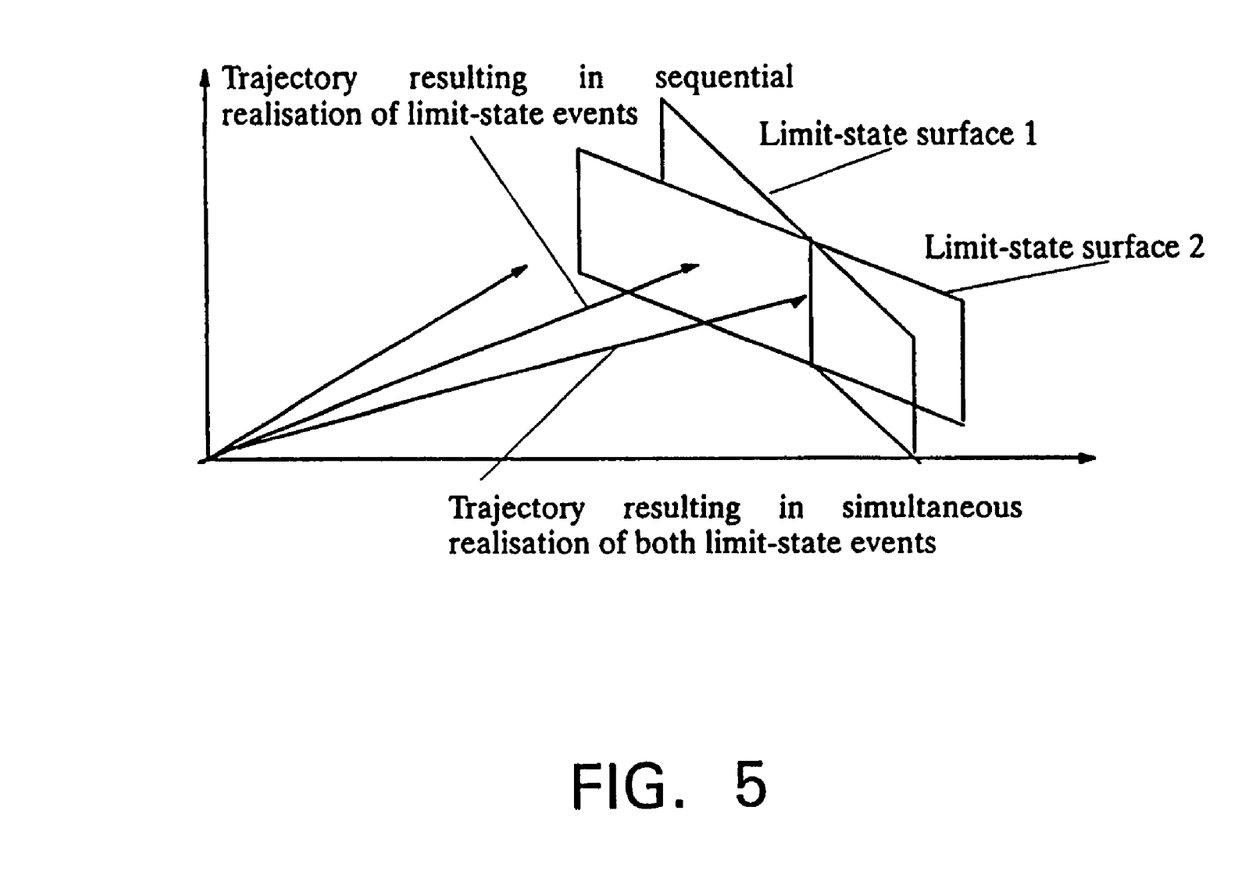
FIG. 5 illustrates trajectories of patient behaviours intersecting multiple event function surfaces in another state subspace.

Processes that are sequential in time are represented by a set of limit-state surfaces that are intersected sequentially by the trajectory see FIG. 5.

Abnormalities of pregnancy can be made visually apparent from sequential intersection of limit-state surfaces rather than simultaneous intersection of the limit-state surfaces. For example, if the 'cervical competence' limit-state surface is intersected before the 'uterine contractions' limit-state surface, then this indicates spontaneous abortion. On the other hand, intersection of the 'uterine contractions' limit-state surface before intersection of the 'cervical competence' limit-state surface can indicate rupture of the uterus.

More complex process controls, involving multiple processes in series and parallel could also be presented geometrically in the state-space, this geometry being characteristic for the process. Further, as each disease has a characteristic set of clinical features, it is suggested that each disease process would have a 'characteristic geometry (or arrangement) of limit-state surfaces' in the chosen state-space, as well as 'characteristic trajectories' in the state-space.

Given this, it is possible to program into the model a vast library of disease state signatures, that is, sets of trajectories and arrangements of limit-state surfaces in defined state-spaces that are characteristic of particular disease states. Given suitable input, the library of disease states could be searched and the closest matches to the known trajectories of a patient being investigated displayed on a computer screen. Further, using statistical methods, the possible disease states for a given set of input data could not only be identified, but arranged in order of probability, from most likely to least likely disease. This could be a valuable clinical tool for the differential diagnosis of disease states.

It is conceivable that the data input to the computer may be at least partially automated. For example, biochemical data could be encoded in bar codes down the side of a laboratory report, while physiological data may be input from electronic monitoring devices. In addition, specific electronic systems may be built into the physical structure of a hospital to facilitate the management of its patients using the method described herein.

Given that there could be a large number of limit-states for a particular disease process, it could be helpful to prioritise or group the limit-states surfaces in some way. For example, limit-state surfaces may be grouped in signs and symptoms of disease commonly employed by clinicians, while another group of limit-state surfaces may be more conveniently employed with biochemical data.

The invention may be easily adapted to include the influence of a drug on anticipated therapeutic outcomes. This influence may be reflected as a change in the shape of the limit-state surface and/or the position within the state-space. It is noted that given sufficient data, a data base of limit-state surfaces for subgroups within a population could be defined in a computer program. For example, women on a particular medication throughout their pregnancy.

In respect of other applications, the management of patients in intensive care could be an example application for the invention. Even after many years of training and practice, it is still very difficult to consider all likely implications when managing a critically ill patient. In this situation, it could be highly beneficial to 'test' a proposed intervention using the method of invention described here. It is easily imagined that the effect of administering a drug to a patient could be trialled on the computer, perhaps by the simple experiment of positioning the cursor on the current position in the state-space, 'clicking' at this position, and then 'dragging' the current position in the state-space to a new location. Even if only one or two subspaces were represented on the computer screen, the effect in 'm' state-subspaces and on 'n' limit-state surfaces could be checked very quickly by calculation. If any limit-state surfaces were found to intersect a trajectory in a state-subspace, the doctor could be alerted, perhaps by a message on the computer screen. The relevant state-subspace could then be viewed on the screen. This procedure can represent an enormous advance over simply trialling the drug in a patient as is presently the case, and perhaps realising too late that some unexpected event has occurred.

EXAMPLE III

Poorly Defined System Behaviour

Even when the system behaviour is very poorly defined, the invention may have some benefits. The state-variables may then be identified as 'risk factors', as they are commonly known. An example is provided by cardiovascular disease. Known risk factors, such as high blood pressure, overweight, family history of heart disease, smoking and high cholesterol may be taken as state variables. For this example, limit-states could be 'heart ischemia' or 'stroke'. The predictive power of the model may be poor, but this only reflects inadequate understanding of the underlying process, and indicates that additional factors are of significance. To further the example of cardiovascular disease, it has recently been established that homocysteine is an important risk factor. With this additional variable comprising the state-space, it is expected that the predictive power of the model would improve. It is evident from this simple example how the latest research data may be incorporated into a model in accordance with the invention, and so it can improve in its role as clinical tool as medical research advances.

Some disease states may be immediately incorporated in the embodiments described here, while others will require more research data. Examples of disease states that could immediately benefit from the approach described here include endocrine diseases, asthma, AIDS and the management of patients in intensive care.

EXAMPLE IV

Representation of Multi-Dimensional Limit State Surface

Rene Descartes represented a function in a 'cartesian plane'. This had simple visual appeal, and by this means, everyone clearly understood what was meant by the term 'function'. A function has one and only one value of the dependent variable 'y' associated with a value of the independent variable 'x'. This can be represented simply by means of a 'cartesian diagram', with 'x' plotted along the horizontal axis and 'y' plotted along the vertical axis.

It is not hard to generalise this result to two independent variables and one dependent variable. In this case, the variables 'x' and 'y' are the independent variables in the horizontal plane, and 'z' is the dependent variable in the vertical direction. In this case, the three dimensional 'cartesian' axes suffice to represent the two independent and one dependent variables. The outcome may be plotted as a two dimensional 'surface', the height above the 'xy' plane representing the magnitude of the dependent variable, or outcome. A line joining equal heights above the plane represent a 'level surface'.

Alternatively, each location in the 'xy' plane may be associated with a number, and a line drawn joining points in the 'xy' plane that are of equal magnitude. Such a map is known as a 'contour' map, and has the advantage of representing a three dimensional surface in only two dimensions (ie. the 'xy' plane). A limit-state surface may be represented by a contour on a contour map.

This is generalisable to four dimensions, the three axes representing the independent variables and the limit-state is represented as a 'level surface' in the three dimensional state-space.

Let there be a function describing a limit-state surface in n dimensional space, viz, $$f=f(X, \ldots, X_n)$$

It is then possible to hold all but three of the independent variables constant. The function is then reduced to four dimensions. These four dimensions are, the three Cartesian axes (forming a state-subspace) and a value associated with each location in the state subspace (note that all the independent variables not in the state subspace are held constant). Now that the dimensionality is reduced, a level surface of function f can be conveniently depicted on a computer screen. Changes in the fourth dimension, i.e. resulting from changes in the values of the independent variables held constant for the representation, can be illustrated by replotting the function f in the three-dimensional state-subspace as altered by those changes. It is noted that more than one surface representing function f could be plotted within one graph to illustrate the dependency of the function f the variables in the state sub-space. This dependency of the function f on the state sub-space variables could be made visually apparent by colour shading in state sub-space or by textual features on the limit surface itself.

If there are twelve independent state variables, then the computer screen could be 'tiled' into four quadrants, and in each quadrant the procedure described in the previous paragraph adopted. That is, each 3-D state-subspace shown in each quadrant would represent the limit-state surface for all but three dependent variables held constant. If the limit-state surface involved the variables in each subspace, then the limit-state surface would be represented in that subspace. The trajectory of the state variables could be depicted in each state-subspace, together with the limit-state surface. Changes of the trajectory and/or the limit-state surface in one state-subspace could then be automatically "transformed" onto the other state-subspaces.

In some circumstances, the dimensionality of the problem may be conveniently reduced by defining a new state variable, $Y_k$ as a function of the state variables $X_i$, viz, $$Y_k=h(X_1, \ldots X_i, \ldots, X_1)$$

This procedure provides a means of systematically structuring medical information (for further details see Example V).

Using the terminology of 'vector geometry', for complex systems, the 'basis' vectors chosen for the n-dimensional state space may not be orthogonal, and that appropriate groupings of the variables may improve orthogonality of the chosen basis vectors. It is further noted that for poorly defined systems appropriate groupings of variables may be indicated by standard statistical techniques eg. factorial analysis. However, orthogonality of the basis vectors is not essential for the method described here to be implemented, given that the system is adequately characterised by research data.

EXAMPLE V

Selection of State-Variables

Figure 6:
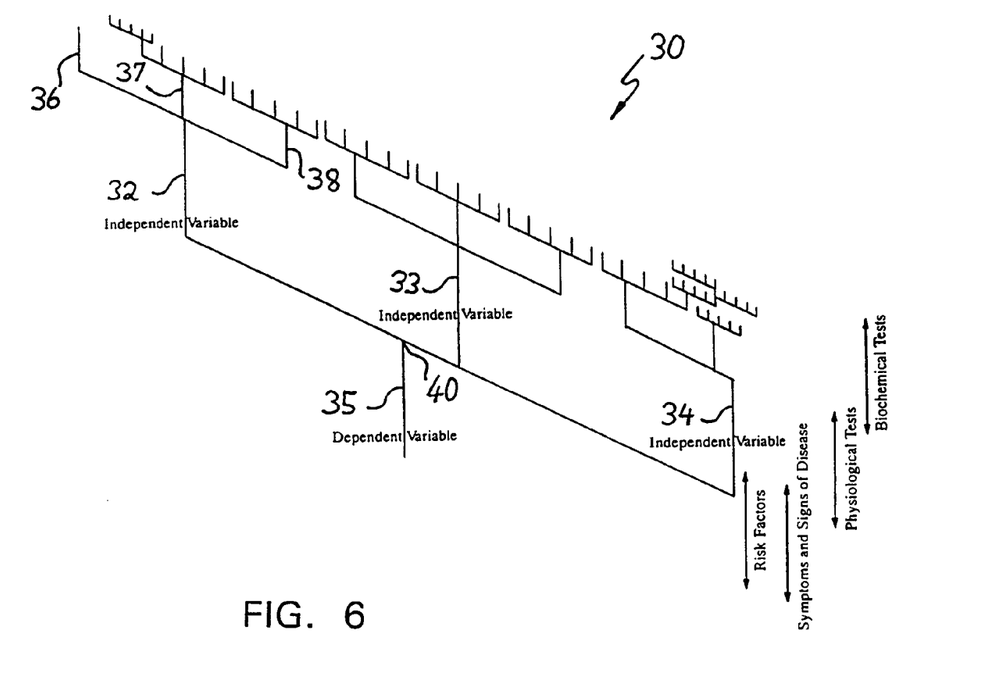
FIG. 6 is a diagram illustrating dependent and independent variables for use in a method in accordance with an embodiment of the present invention.

A 'causation tree' 30 (see FIG. 6) can provide a systematic approach for the identification and arrangement of state-variables, thereby providing a means for structuring the system information.

Having chosen a dependent variable that is appropriate for the limit-state being investigated, a causation tree 30 may be constructed, showing all 'independent' state-variables 32, 33, 34 contributing to the value of the dependent variable 35. Each 'independent' state-variable may be viewed in turn as a dependent variable each with its own set of state-variables, e.g. 36, 37, 38. Hence each 'branch point', e.g. 40 is the starting point for another set of state-variables. This process may be geometrically represented as the 'causation tree' 30 (see FIG. 6). It is noted that system complexity is qualitatively conveyed by the number of branches at each level. Further it is noted that interactions between variables is systematically represented in the 'causation tree' by variables appearing more than once (hence state-variables may not be independent).

This structuring of information using a 'causation tree' provides a systematic means for identifying the state-variables employed in the mathematical model.

Well understood systems may be described in terms of the known variables. Poorly understood systems, or partly defined systems, may be defined in terms of new variables that represent groupings of variables. Established statistical methods are available for establishing the most appropriate variable groupings eg. factorial analysis.

The variables chosen for representation in the model described here may depend on the time scale over which the process evolves. For example, a 'glucose tolerance test' may evolve over a period of hours, while an investigation of diabetes may evolve over a period of years or decades. Different state-variables may be chosen for the analysis of the same system, depending on the time scale involved, thereby providing further means for systematically structuring system/medical information.

The previous paragraphs indicate that the state-variables chosen for an analysis are somewhat arbitrary, in that the state-variables employed must only lie further along the 'causation tree'. The actual variables chosen for measurement will therefore be dependent on many factors such as the state of knowledge, convenience of data collection, established medical practice, costs and other practical constraints associated with gathering data.

EXAMPLE VI

Applicability to 'Normal' States

The present invention may also be applied to monitor the evolution of a biological system towards a normal state. For example, the fitness level of an athlete training for a particular short term or long term goal could be improved utilising the present invention. In that embodiment, the limit-state surface would define a predetermined fitness level within a multi-dimensional space. The variables of the multi-dimensional space could include resting heart rate, 'stressed' heart rate, resting breathing rate, 'stressed' breathing rate, isotonic and isometric muscle strength, haemoglobin concentration in the blood. The athlete's progress could then be monitored utilising a trajectory within the appropriate multi-dimensional space. The analysis and displaying of the trajectory and the limit-state surface could substantially be the same as described in the previous examples. In the particular example of the athlete preparing for a short or long term goal, previous trajectories of "successful" athletes during their preparation/training could be used to guide/evaluate the development of the athlete currently monitored.

The claims defining the invention are as follows:

1. A computer based method of analysing an evolution of a biological system comprising:
   determining a series of variables upon which a state of the biological system depends;

mapping the variables to an n-dimensional space, where n is an integer greater than 2;

monitoring and displaying the evolution of the biological system utilising at least one trajectory formed from sets of the variables of the biological system at different times, thereby using time as a parameter in the n-dimensional space in a manner such that every point on the trajectory corresponds to at least one value of time;

evaluating and displaying the evolution of the biological system as indicated by the trajectory utilising different sets of predetermined values of the variables to formulate first and second n-dimensional surfaces representing respective first and second different predetermined states of the biological system within the n-dimensional space; and predicting or projecting for [diagnosis or prognosis] a progression of the trajectory to the first and second surfaces for indicating the normality or abnormality of the evolution of the biological system.

2. A computer arranged to analyse an evolution of a biological system based on series of variables upon which a state of the biological system depends, the computer being arranged to:

map a first subset of the variables to a first n-dimensional sub-space;

map a second subset of the variables to a second n-dimensional sub-space;

monitor and display the evolution of the biological system based on trajectories formed from sub-sets of the variables which define the states of the biological system at different times; and evaluate and display the evolution of the biological system as indicated by the trajectories utilising sets of predetermined values of the variables to formulate at least one n-dimensional surface representing a predetermined state of the biological system within each of the n-dimensional sub-spaces.

3. A computer as claimed in claim 2, wherein the evaluating comprises predicting a progression of at least one of the trajectories.

4. A computer as claimed in claim 2 wherein n is an integer greater than 2.

5. A computer as claimed in claim 3, wherein the computer is arranged to base the prediction of the progression of the at least one trajectory on the previous development of the trajectory within at least one of the n-dimensional sub-spaces.

6. A computer as claimed in claim 3, wherein the computer is arranged to predict the progression of one of the trajectories on the basis of at least one other of the trajectories determined in the n-dimensional sub-spaces.

7. A computer as claimed in claim 2, wherein the computer is further arranged to depict a speed of at least one of the trajectories along the trajectory.

8. A computer readable storage medium comprising instructions to control a computer to analyse an evolution of a biological system based on series of variables upon which a state of the biological system depends, the instructions comprising instructions to control the computer to:

map a first subset of the variables to a first n-dimensional space;

map a second subset of the variables to a second n-dimensional space;

monitor and display the evolution of the biological system based on trajectories formed from sub-sets of the variables which define the states of the biological system at different times; and evaluate and display the evolution of the biological system as indicated by the trajectories utilising sets of predetermined values of the variables to formulate at least one n-dimensional surface representing a predetermined state of the biological system within the n-dimensional subspaces.

9. A computer readable storage medium as claimed in claim 8, wherein the evaluating comprises predicting a progression of the trajectory to the n-dimensional surface.

10. A computer readable storage medium as claimed in claim 8, wherein n is an integer greater than 2.

11. A computer readable storage medium as claimed in claim 9, wherein the instructions further comprise instructions to control the computer to base the prediction of the progression of at least one of the trajectories on the previous development of the trajectory within the n-dimensional space.

12. A computer readable storage medium as claimed in claims 9 or 11, wherein the instructions further comprise instructions to control the computer to predict the progression of the trajectory on the basis of other trajectories determined in the n-dimensional space.

13. A computer readable storage medium as claimed in claim 8, wherein the instructions further comprise instructions to control the computer to depict a speed of at least one of the trajectories along the trajectory.

* * * * *